US005773717A

United States Patent [19]

Reinhardt et al.

[11] Patent Number: 5,773,717
[45] Date of Patent: Jun. 30, 1998

[54] APPARATUS AND RELATED METHODS FOR DETERMINING LATERAL TIRE TREAD STIFFNESS

[75] Inventors: Andrew K. Reinhardt, Akron; Stephen M. Vossberg, Uniontown; David O. Stalnaker, Hartville; John L. Turner, Akron, all of Ohio

[73] Assignee: Bridgestone/Firestone, Inc., Akron, Ohio

[21] Appl. No.: 733,374

[22] Filed: Oct. 17, 1996

[51] Int. Cl.⁶ .......................... G01M 17/02; G01N 3/24
[52] U.S. Cl. .......................... 73/146; 73/841; 73/843
[58] Field of Search .......................... 73/146, 8, 841, 73/843, 794

[56] References Cited

U.S. PATENT DOCUMENTS

| | | | |
|---|---|---|---|
| 3,589,182 | 6/1971 | Burgett | 73/146 |
| 3,681,980 | 8/1972 | Decker | 73/794 |
| 3,722,270 | 3/1973 | Sperberg | 73/146 |
| 3,948,095 | 4/1976 | Bergett et al. | 73/146 |
| 4,028,937 | 6/1977 | Crano | 73/146 |
| 4,622,848 | 11/1986 | Doi | 73/146 |
| 4,682,504 | 7/1987 | Kobayashi | 73/794 X |
| 4,821,582 | 4/1989 | Meyer et al. | 73/862.04 |
| 4,986,118 | 1/1991 | Pottinger | 73/146 |
| 5,113,688 | 5/1992 | Lazeration | 73/146 X |
| 5,460,036 | 10/1995 | Church | 73/146 |

*Primary Examiner*—George M. Dombroske
*Assistant Examiner*—Joseph L. Felber
*Attorney, Agent, or Firm*—Carmen S. Santa Maria

[57] ABSTRACT

An apparatus for determining lateral tire tread stiffness includes a holding fixture that is coupled to a loading fixture. The holding fixture includes a frame on which is mounted a rotary table that carries the tire tread specimen to be tested. The loading fixture includes a loading plate that can apply a normal loading force and a lateral loading force to the tire tread specimen. A processor receives data from a monitoring device which provides an indication of the deformation of the tire tread specimen as a lateral load is applied thereto. The processor also receives data from a load cell which monitors the amount of force applied to the tread specimen and correlates this data with the displacement data to determine stiffness properties of the tread specimen. The processor also controls the angular position of the rotary table to further analyze the tread stiffness of particular tire tread geometry.

14 Claims, 2 Drawing Sheets

APPARATUS AND RELATED METHODS FOR DETERMINING LATERAL TIRE TREAD STIFFNESS

TECHNICAL FIELD

The invention herein resides generally in the art of tire testing equipment. More particularly the present invention relates to an apparatus and related methods for measuring the stiffness of a tire tread and components thereof. Specifically, the present invention relates to an apparatus and related methods for measuring tire tread stiffness by applying a normal force and then a lateral force to a tire tread in a plurality of angular increments

BACKGROUND OF THE INVENTION

It is generally known that tire performance or the "ride" of the tire is attributable to many factors, such as tire shape, inflation pressure, construction of the tire, and the materials used to manufacture the tire, to name a few. Tires are designed to provide a smooth quiet ride with minimal vibration and with minimal exertion of force from the driver to control the direction of the car on which the tires are mounted. These ride characteristics are directly attributable to the tread design and the material used to manufacture the tire. To assist in analyzing tread design, various testing devices have been developed to correlate deflection of the tread ribs to wear rate and for measuring tire force and tire tread motion in a common area of the tire.

U.S. Pat. No. 4,028,937, entitled "Nondestructive Testing Of Tire Wear," discloses a method and apparatus for qualitatively determining tire wear of pneumatic tires. This patent discloses statically loading the shoulder ribs and adjacent ribs of a tire tread with deflection members that are mounted to at least one strain gauge. The strain gauge generates a deflection value, wherein the greater deflection value corresponds to a greater wear rate. Although this invention is effective in its stated purpose, it only monitors deflection of the tire tread in one direction and does not consider additional forces applied in other directions.

Another apparatus for testing tire characteristics is disclosed in U.S. Pat. No. 4,986,118, entitled "Apparatus For Measuring Tire Tread Force and Motion." The apparatus of this invention measures tire force and tire tread motion in a common area of a tire under test. A tire is rolled over a tire test block which has a plurality of sensors attached to strain gauges which measure characteristics, indicative of the tire force and tread motion. Although this invention is effective in its stated purpose, it still does not provide a consideration of the total impact of the tire tread and its associated lug geometry.

The aforementioned patents and other testing equipment do not appreciate the impact of tread geometry on the car ride and, in particular, the effect of tread geometry on tread stiffness and tire cornering force or aligning torque. In other words, known tire testing apparatuses are deficient in considering tread and lug designs which cause drift or pull when driving an automobile with the subject tires.

Based upon the forgoing, it is evident that there is a need in the art for test equipment and related methods for using the same that provide test data of the effects of tread and lug design. Moreover, there is a need in the art for a testing device and method for using the same that analyzes lateral stiffness of a tread and lug design. There is also a need for test equipment that measures the lateral stiffness of treads and lugs at a plurality of angular increments.

SUMMARY OF INVENTION

In light of the foregoing it a first aspect of the present invention to provide an apparatus and related methods for determining tire tread stiffness.

Another aspect of the present invention is to provide a device that determines the lateral stiffness of a tire tread and its associated tread lug design.

Still a further aspect of the present invention, as set forth above, is to provide a testing device which includes a rotary table upon which is mounted a tread test specimen that can be rotated at predetermined angular increments.

An additional aspect of the present invention, as set forth above, is to provide a loading plate which applies a normal and a lateral force to the tire tread specimen.

Yet an additional aspect of the present invention, as set forth above, is to provide a measuring device that detects the lateral movement of the loading plate as a lateral force is applied to the tire tread specimen.

A further aspect of the present invention, as set forth above, is to provide a load cell which monitors both the lateral force and the normal force applied during the lateral movement of the loading plate.

Another aspect of the present invention, as set forth above, is to provide a processor which correlates the lateral movement measurements and the lateral forces applied to the tire tread specimen to derive a tread stiffness value.

Yet a further aspect of the present invention, as set forth above, is to provide a bi-axial load frame which applies an oscillating lateral force at a frequency ranging from about 1 hertz to about 10 hertz and at about 5% to about 10% lateral shear strain.

The foregoing and other aspects of the invention which shall become apparent as the detailed description proceeds, are achieved by an apparatus for measuring tread stiffness, comprising: a table for carrying a tread specimen; a loading plate coupled to the tread specimen, the loading plate movable in at least two directions; means for determining an amount of force applied by the loading plate; and means for measuring an amount of displacement to the tread specimen when the loading plate is moved.

The present invention also provides an apparatus for determining lateral stiffness in a specimen comprising: means for holding a specimen; means for applying a lateral load to the specimen; means for measuring a movement of the specimen while the lateral load is applied thereto; and means for processing the movement of the specimen and the amount of the lateral load to determine a lateral stiffness of the specimen.

Other objects of the present invention are also provided by a method for determining the lateral stiffness of a tire tread specimen, comprising the steps of: mounting a tire tread specimen on a table; applying a normal load to the tire tread specimen; applying a lateral load to the tire tread specimen; measuring an amount of lateral displacement of the specimen as the lateral load is applied thereto; and calculating a lateral stiffness value of the tire tread specimen.

BRIEF DESCRIPTION OF THE DRAWINGS

For a complete understanding of the objects techniques and structure of the invention, reference should be made to the following detailed description and accompanying drawings wherein.

PREFERRED EMBODIMENT FOR CARRYING OUT THE INVENTION

Figure 1:
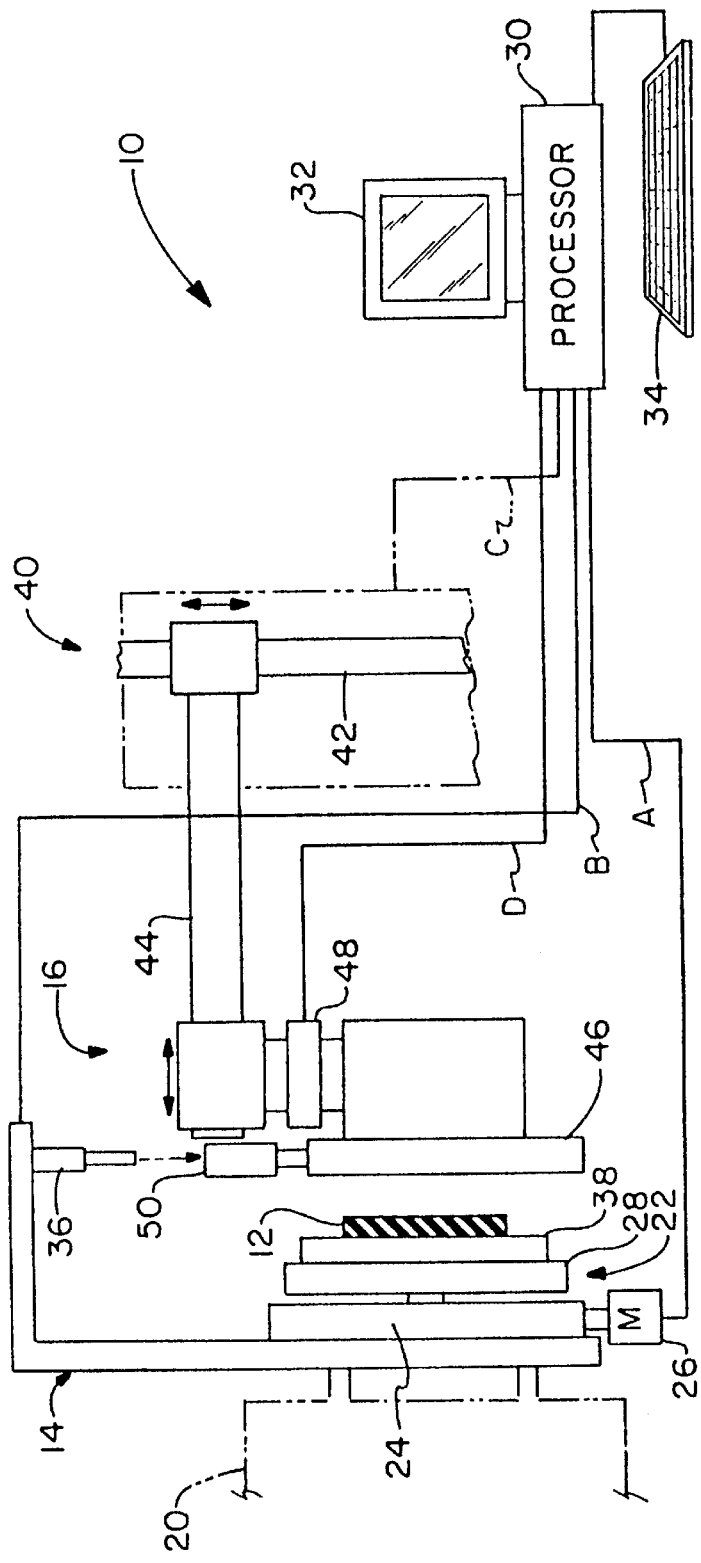
FIG. 1 is a top schematic view of an apparatus for determining tire tread stiffness.

Referring now to the drawings and more particularly to FIG. 1, it can be seen that an apparatus for determining tire tread stiffness is designated generally by the numeral 10. Generally, the apparatus 10 applies normal and lateral forces to a tire tread specimen 12 so that lateral stiffness values of the specimen can be determined. The tire tread specimen 12 has a maximum size of about 8 inches×11 inches. It will be appreciated that the tire tread specimen 12 may also be a tread lug which is siped, non-siped or a series of tread lugs or any configuration of a specimen which includes a portion of a tire tread in which the tread element stiffness needs to be determined. The specimen 12 may include the underlying construction of the tire such as belts and cord-reinforced plies.

A holding fixture 14 carries the tire tread specimen 12 while a loading fixture 16 is coupled thereto. The holding fixture 14 is a substantially stationary device while the loading fixture 16 applies normal and lateral loads to the tire tread specimen 12. The loading fixture 16 functions to first apply a normal load and then a lateral or shearing load to the tire tread specimen 12. In the preferred embodiment, the loading fixture 16 can apply a normal force of up to about 3500 lbf and a lateral force of up to about 1400 lbf.

The holding fixture 14 includes a frame 20 which is a stationary fixed object that can withstand the loading forces generated by the loading fixture 16. Secured to the frame 20 is a rotary table 22 which includes a base 24. A motor 26 is mounted on the base 24 and functions to rotate a platter 28 in predetermined angular increments. As will be discussed in further detail hereinbelow, the rotation of the platter 28 allows for different orientations of the tread specimen 12 when a lateral force is applied thereto.

A processor 30, which contains the necessary hardware, software and memory to control the operation of the apparatus 10, is connected to the motor 26 to control the operation of the platter 28. As seen in FIG. 1, the processor 30 is connected to the motor 26 by the lead line with the capital letter designation A. Connections between the processor 30 and other components within the apparatus 10 are designated by like capital letter designations. Also connected to the processor 30 is a display monitor 32 which provides a visual indication of the operational status of the apparatus 10 and a keyboard 34 which allows an operator to provide input instructions to the apparatus 10. It will be appreciated that the processor 30 controls the application of force applied by the loading fixture 16 and collects and stores the output test data generated by the apparatus 10 for analyzing the tire tread specimen 12.

A displacement monitoring device 36, which may be mounted between the frame 20 and the base 24, is connected to the processor 30 for measuring movement of a reference point located on the loading fixture 16. In the preferred embodiment, the monitoring device 36 is a laser range finder which projects a laser light and correlates the reflection thereof to a quantifiable distance. Of course, other known measuring devices such as rulers, ultrasonic sensors and the like may be used for the monitoring device 36.

A specimen plate 38 is fastenably secured to the platter 28 by threaded bolts or other such fastening devices. The tire tread specimen 12 may be adhesively secured to the specimen plate 38 and in such a manner that the normal and lateral forces applied thereto do not loosen the tire tread specimen 12 from the specimen plate 38.

The loading fixture 16 includes a bi-axial load frame 40 which is hydraulically actuated and controlled by the processor 30. FIG. 1 only presents a partial representation of the bi-axial load frame 40, but as those skilled in the art will appreciate it performs the necessary functions for coupling the loading fixture 16 to the holding fixture 14. The bi-axial load frame 40 includes a lateral loading arm 42 and a normal loading arm 44. A loading plate 46, which is movable in at least two directions, extends from the normal loading arm 44. Specifically, the lateral loading arm 42 functions to move the loading plate 46 in a lateral direction with respect to the tire tread specimen 12. The normal loading arm 44 functions to move the loading plate in a normal direction and apply a normal loading force to the tire tread specimen 12. A load cell 48 is disposed between the loading plate 46 and the normal loading arm 44 to detect and monitor both the normal and lateral forces applied to the tire tread specimen 12. The load cell 48 is connected to the processor 30 which collects the force values applied to the tire tread specimen 12 by the bi-axial load frame 40.

A displacement bar 50 is mounted to the loading plate 46 in juxtaposition to the monitoring device 36. As those skilled in the art will appreciate, the lateral movement of the displacement bar 50 correlates to the lateral movement of the loading plate 46 when a lateral load force is applied to the tire tread specimen 12. Accordingly, the monitoring device 36 monitors the displacement of the tire tread specimen 12 as a lateral force is applied thereto. The displacement bar 50 may be mounted anywhere on the loading fixture 16 that provides a positive indication of the lateral deflection of the tire tread specimen 12 under lateral load. Moreover, it will be appreciated that the mounting positions of the displacement bar 50 and the monitoring device 36 could be switched so that the monitoring device 36 monitors its own movement with respect to the displacement bar 50 or other fixed reference. This switch still provides an indication of the lateral deflection of the tire tread specimen 12 under load.

Figure 3:
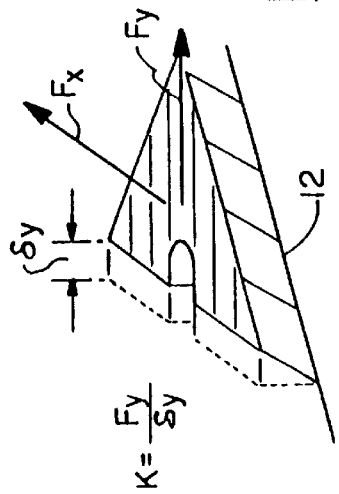
FIG. 3 is a representation of a tire lug which is employed to determine tread anisotropic stiffness.
Figure 2:
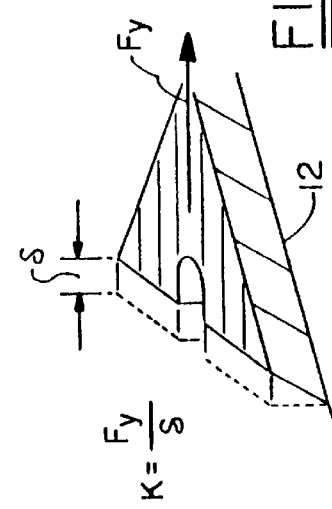
FIG. 2 is a representation of a tire lug exposed to a lateral load.
Figure 5:
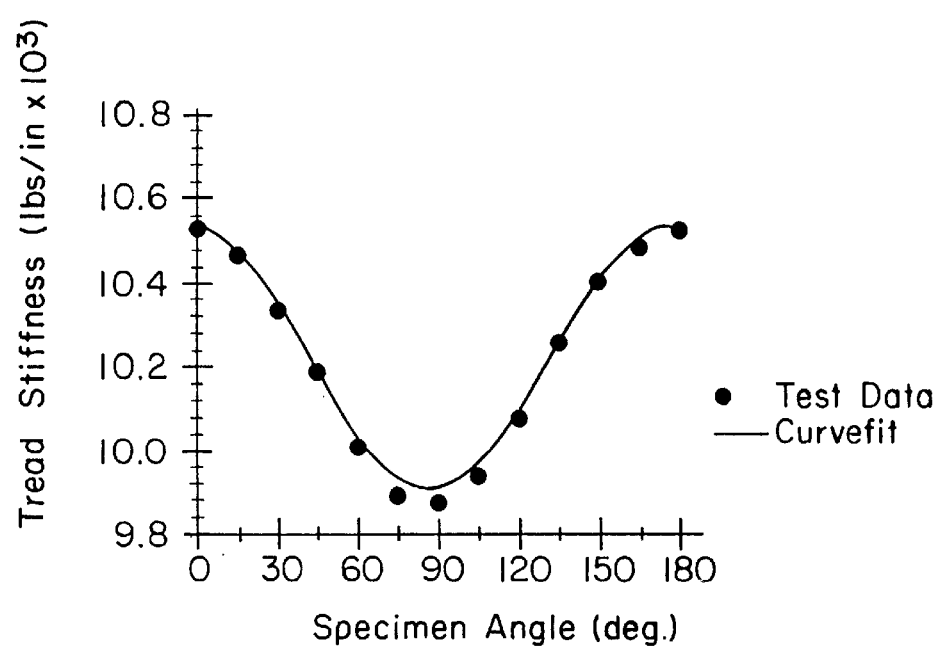
FIG. 5 is a graphical representation of tread stiffness data.

Referring now to FIGS. 2 and 3, it can be seen that when a lateral force $F_y$ is applied to a tire tread specimen 12 a force constant of the tire tread specimen can be derived. In particular, a constant K is derived from the ratio of force ($F_y$) to elongation ($\delta$) where $\delta$ is equal to the lateral displacement of the tread specimen under lateral load. Those skilled in the art will appreciate that the constant K is indicative of the stiffness of the material used to manufacture the tire tread specimen and more importantly, an indication of the stiffness of the tire tread geometry. By rotating the tread specimen 12 and then applying a lateral load, a tread anisotropic stiffness can be derived as seen in FIG. 3 & 5. By determining tread stiffness anisotropy, the designs of tread lugs can be examined to evaluate their effect on the tire residual aligning torque and the tire cornering coefficients. In other words, the anisotropy stiffness valves can be analyzed to see what impact a tread design has on the directional pull of the tire.

Figure 4:
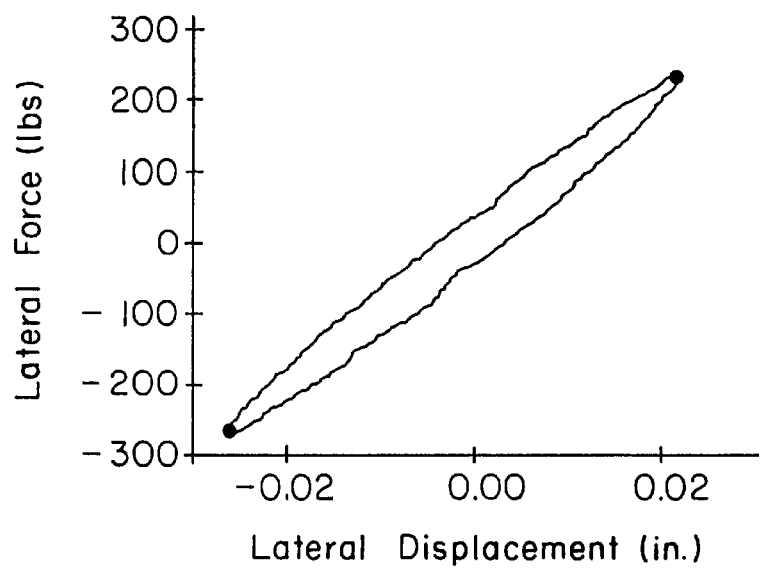
FIG. 4 is a graphical representation of a loading of a tire tread specimen.

To generate values for the above variables, an operator adhesively bonds or secures by other means the tire tread specimen 12 to the specimen plate 38. The operator then secures the specimen plate 38 to the platter 28 of the rotary table 22. The processor 30 stores the particular angle at which the platter 28 is situated prior to coupling the loading fixture 16 to the holding fixture 14. Upon actuation of the loading fixture 16, the normal loading arm 44 applies a normal load to the tire tread specimen 12 to simulate the weight of a vehicle or other device that would apply a load to a specimen. After the normal load is applied to the tire tread specimen 12, the lateral loading arm 42 applies a lateral shear strain to the tire tread specimen 12 of about 3% to 20% and typically between 5% to 10%. The lateral loading arm 42 is oscillated at a selected frequency of about 0.1 hertz to about 10 hertz which generates an elongation or lateral displacement value with respect to the lateral force applied as shown by the graph in FIG. 4. Generally, a lower frequency is selected when a higher lateral shear strain is applied to the tire tread specimen 12. The frequency and shear strain are adjusted inversely: as one is increased, the other is decreased, to control strain rate and to eliminate the prospect of slip on the tread elements. Those skilled in the art will appreciate that the graph shown in FIG. 4 is a stress-strain curve for a sample tire tread specimen 12. This curve is also commonly referred to a hysteresis loop. The processor 30 monitors the forces applied and the displacement values for each lateral force and stores these values accordingly. After the lateral force cycle has been applied for a predetermined number of times, the applications of the lateral force and the normal force are withdrawn. At this time, the processor 30 instructs the platter 28 to rotate a predetermined angular increment, which in the preferred embodiment is about 15°. The processor 30 instructs the bi-axial load frame 40 to re-apply the normal and lateral loading forces as above and collects the resulting data. This is continued until the desired data is collected or until the platter 28 is rotated a complete revolution. The data collected can then be plotted on a graph as shown in FIG. 5 which compares the orientation angle of the tire tread specimen 12 with the resulting tread stiffness calculated in lbf/in. FIG. 5 presents a substantially sinusoidal curve that demonstrates the variations in tread stiffness values as the tire tread specimen 12 is rotated by the rotary table 22. Tire performance can then be altered by manipulating the values of the maximun and minimum tread stiffnesses, through lug design and material selection.

It is apparent then from the above description of the operation and methods of use for the apparatus 10 that the problems associated with previous tire testing equipment have been overcome. In particular, the apparatus 10 provides a device that rotates the tread geometry in a way that heretofore has been unavailable. The apparatus 10 is also capable of determining what impact different materials with a particular tread geometry design have on tread stiffness. This test data facilitates tire designers in determining residual aligning torque predictions and cornering predictions of a tire tread design. The data obtained by the apparatus 10 can also be employed to verify finite element analysis and other tread stiffness calculations. As such, the apparatus 10 provides additional information that can be employed by a tire designer to make better handling and safer tires for the general public.

Thus, it can be seen that the objects of the invention have been satisfied by the structure presented above. It should be apparent that the apparatus 10 can be adapted for use in analyzing any specimen that undergoes normal and lateral loading forces.

While the preferred embodiment of the invention has been presented and described in detail, it will be understood that the invention is not limited thereto or thereby. Accordingly, for an appreciation of the true scope and breadth of the invention, reference should be made to the following claims.

What is claimed is:

1. An apparatus for measuring tread stiffness, comprising:
    a table for carrying a tread specimen;
    a loading plate coupled to the tread specimen, said loading plate movable in at least two directions;
    means for determining an amount of force applied by said loading plate;
    means for measuring an amount of displacement to the tread specimen when said loading plate is moved; and
    means for processing said amount of force and said amount of displacement to determine the stiffness of the tread specimen, said processing means controlling the movement of said loading plate.

2. The apparatus according to claim 1, further comprising:
    a frame upon which said table is mounted, said table rotatable with respect to said frame.

3. The apparatus according to claim 2, wherein said measuring means comprises:
    a distance monitor mounted to one of said loading plate and said frame; and
    a displacement bar mounted to the other of said loading plate and said frame, said distance monitor measuring the movement of said displacement bar which correlates to the displacement of the tread specimen.

4. The apparatus according to claim 3, wherein said loading plate applies a normal force to the tread specimen in one direction and a lateral force to the tread specimen in the other direction.

5. The apparatus according to claim 4, wherein said loading plate is oscillated in one direction at a frequency of from about 0.1 hertz to about 10 hertz.

6. An apparatus for determining lateral stiffness in a specimen, comprising:
    means for rotatably holding a specimen;
    means for applying a lateral load to the specimen;
    means for measuring a movement of the specimen while said lateral load is applied thereto; and
    means for processing the movement of the specimen and the amount of said lateral load to determine a lateral stiffness of the specimen, said processing means alternatingly rotating said rotatably holding means and applying said lateral load.

7. The apparatus according to claim 6, wherein said rotatably holding means comprises:
    a frame;
    a rotary table rotatable in angular increments and carried by said frame;
    a mounting fixture carried by said rotary table to hold the specimen, said processing means controlling the operation of said rotary table and said applying means.

8. The apparatus according to claim 6, wherein said applying means comprises:
    a loading plate;
    first means for moving said loading plate in a first direction; and
    second means for moving said loading plate in a second direction orthogonal to said first direction, said processing means controlling the operation of said first and said second moving means to couple said loading plate to the specimen.

9. The apparatus according to claim 6, wherein said measuring means comprises:
    a distance monitor mounted to one of said holding means and said applying means; and
    a displacement bar mounted to the other of said holding means and said applying means, said distance monitor measuring the movement of said displacement bar which correlates to the lateral stiffness of the specimen.

10. A method for determining the lateral stiffness of a tire tread specimen, comprising the steps of:
    mounting a tire tread specimen on a table;

applying a normal load to the tire tread specimen;

applying a lateral load to the tire tread specimen;

measuring an amount of lateral displacement of the specimen as said lateral load is applied thereto; and calculating a lateral stiffness value of the tread specimen.

11. The method according to claim 10, wherein said step of applying a lateral load comprises the steps of:

oscillating said lateral load at a frequency of from about 0.1 hertz to about 10 hertz; and imparting a shear strain to the tire tread specimen of between about 3% to about 20%.

12. The method according to claim 11, further comprising the steps of:

a) rotating said table a predetermined angular increment;

b) applying said normal load to the tire tread specimen;

c) applying said lateral load to the tire tread specimen;

d) measuring said amount of lateral displacement;

e) removing said normal load and said lateral load from the tire tread specimen; and f) repeating steps a) through e) until said table is rotated about a complete revolution.

13. The method according to claim 12, wherein said step of measuring further comprises the steps of:

affixing a monitoring device to one of said table and said lateral load; and affixing a monitored device to the other of said table and said lateral load.

14. An apparatus for determining lateral stiffness in a specimen comprising:

means for holding a specimen;

means for applying a lateral load in a first direction and in a second direction orthogonal to said first direction, wherein the movement of said applying means in one direction is independent of the movement in the other direction;

means for measuring a movement of the specimen while said lateral load is applied thereto; and means for processing the movement of the specimen and the amount of said lateral load to determine a lateral stiffness of the specimen.

* * * * *